United States Patent [19]

Ishida et al.

[11] Patent Number: 5,425,729
[45] Date of Patent: * Jun. 20, 1995

[54] LASER COAGULATION SYSTEM

[75] Inventors: Makoto Ishida, Gamagori, Japan; Donald T. McCallum, Anderson, Calif.; Chikashi Koike, Hino, Japan; Stephan Pataki, Campbell, Calif.

[73] Assignees: Kowa Company Ltd.; Coherent Incorporated, both of Japan

[*] Notice: The portion of the term of this patent subsequent to Jul. 26, 2005 has been disclaimed.

[21] Appl. No.: 853,340

[22] Filed: Mar. 16, 1992

Related U.S. Application Data

[63] Continuation of Ser. No. 769,332, Sep. 30, 1991, abandoned, which is a continuation of Ser. No. 657,243, Feb. 14, 1991, abandoned, which is a continuation of Ser. No. 499,558, Mar. 26, 1990, abandoned, which is a continuation of Ser. No. 364,487, Jun. 9, 1989, abandoned, which is a continuation of Ser. No. 253,392, Oct. 3, 1988, abandoned, which is a continuation of Ser. No. 919,318, Oct. 14, 1986, abandoned.

[30] Foreign Application Priority Data

Oct. 18, 1985 [JP] Japan .................................. 60-231315

[51] Int. Cl.⁶ .............................................. A61N 5/06
[52] U.S. Cl. ............................................ 606/13; 606/4
[58] Field of Search ................... 128/395, 397, 398; 606/2, 4–6, 10–19

[56] References Cited

U.S. PATENT DOCUMENTS

| | | | |
|---|---|---|---|
| 2,699,092 | 1/1955 | Rantsch . | |
| 3,828,788 | 8/1974 | Krasnov et al. | 128/303.1 |
| 4,091,814 | 5/1978 | Togo | 128/303.1 |
| 4,164,222 | 8/1979 | Prokhorov et al. | 128/303.1 |
| 4,215,694 | 8/1980 | Isakov et al. | 128/303.1 |
| 4,428,035 | 1/1984 | Muller et al. | 362/224 |
| 4,460,943 | 7/1984 | Callahan | 362/451 |
| 4,477,720 | 10/1984 | Pearson | 250/201 |
| 4,478,217 | 10/1984 | Shimada et al. | 606/13 |
| 4,499,897 | 2/1985 | Roussel | 128/303.1 |
| 4,503,854 | 3/1985 | Jako | 128/303.1 |
| 4,520,816 | 6/1985 | Scharchar et al. | 606/11 |
| 4,520,824 | 6/1985 | Swaniger et al. | 128/395 |
| 4,526,447 | 7/1985 | Taylor | 606/18 |
| 4,545,713 | 10/1985 | Beni et al. | 128/303.1 |
| 4,552,360 | 11/1985 | Bromley et al. | 273/148 B |
| 4,561,436 | 12/1985 | Munnerlyn | 128/303.1 |
| 4,580,557 | 4/1986 | Hertzmann et al. | 606/12 |
| 4,586,079 | 4/1986 | Cooper, Jr. et al. | 358/100 |
| 4,597,380 | 7/1986 | Raif et al. | 128/303.1 |
| 4,648,400 | 3/1987 | Schneider et al. | 606/5 |
| 4,712,208 | 12/1987 | Dolby | 369/128 |
| 4,736,744 | 4/1988 | Koike et al. | 128/303.1 |
| 4,759,360 | 7/1988 | Nakanishi et al. | 606/6 |
| 4,776,335 | 10/1988 | Nakanishi et al. | 606/17 |

FOREIGN PATENT DOCUMENTS

| | | | |
|---|---|---|---|
| 355996 | 2/1990 | European Pat. Off. | 606/7 |
| 2611933 | 9/1977 | Germany | 128/303.1 |
| 3723227 | 10/1988 | Germany | 606/16 |
| 3833361 | 4/1990 | Germany | 604/264 |
| 1052232 | 11/1983 | U.S.S.R. | 606/4 |
| 8403220 | 8/1984 | WIPO | 128/303.1 |
| 8700748 | 2/1987 | WIPO | 606/5 |
| 8803005 | 5/1988 | WIPO | 606/15 |

Primary Examiner—David M. Shay
Attorney, Agent, or Firm—Bruce L. Adams; Van C. Wilks

[57] ABSTRACT

An apparatus for ophthalmic laser treatment of the eye of a patient has a slit image projector which projects a slit image along a common optical axis into the eye of a patient to illuminate the eye, and a laser beam projector which projects a laser beam spot along the common optical axis into the eye of the patient to treat the eye. A common reflector is disposed on the common optical axis for selectively reflecting the slit image and the laser beam spot toward the eye. The reflector has one section positioned to reflect and direct the slit image toward the eye to illuminate the eye, and another section driveably displaceable relative to said one section to reflect and direct the laser beam spot toward the eye to thereby scan the laser beam spot relative to the slit image. Observation equipment is used for observing the slit image and the laser beam spot projected into the eye of the patient to determine the portion of the eye to be treated with reference to the slit image. A manipulator is operated while the laser beam spot is being observed for driving the other section of the reflector to enable the same to scan the laser beam spot within the determined portion of the eye to carry out the ophthalmic laser treatment.

14 Claims, 8 Drawing Sheets

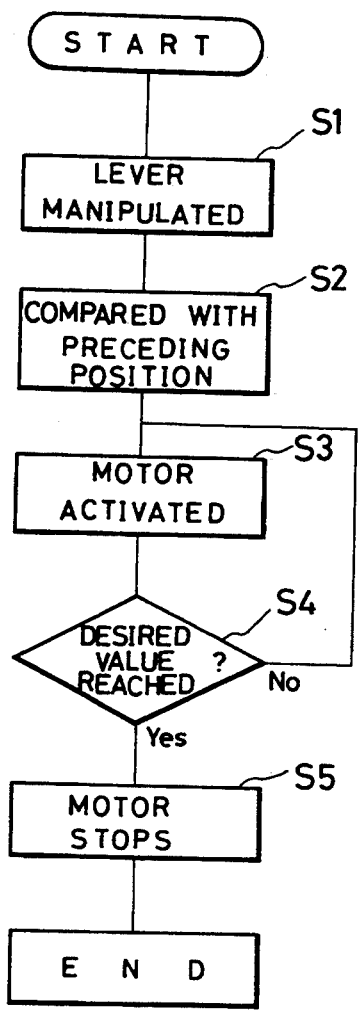
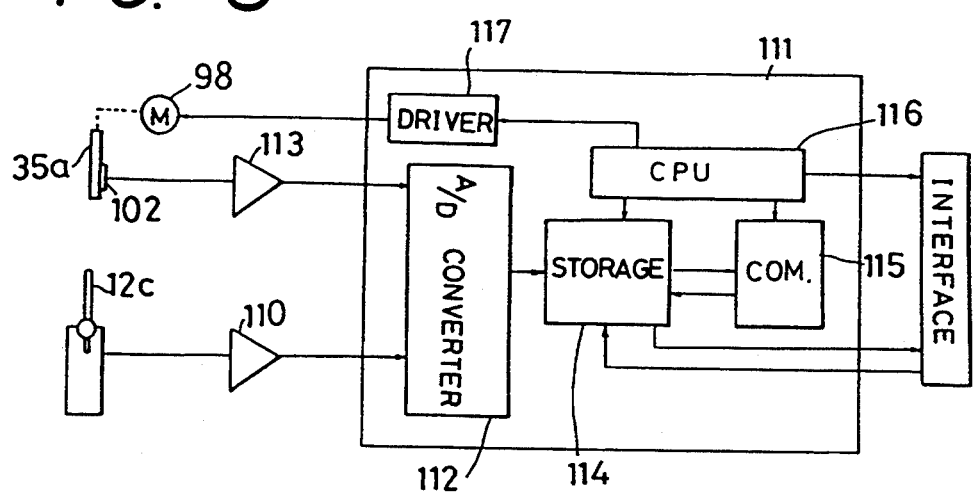

LASER COAGULATION SYSTEM

This is a continuation application of Ser. No. 7669,332 filed Sept. 30, 1991, now abandoned, which is a continuation application of Ser. No. 657,243 filed Feb. 14, 1991, now abandoned, which is a continuation application of Ser. No. 499,558 filed Mar. 26, 1990, now abandoned, which is a continuation application of Ser. No. 364,487 filed Jun. 9, 1989, now abandoned, which is a continuation application of Ser. No. 253,392 filed Oct. 3, 1988, now abandoned, which is a continuation application of Ser. No. 919,318 filed Oct. 14, 1986, now abandoned.

BACKGROUND OF THE INVENTION

1. Field of the Invention

This invention relates to a laser coagulation system, and more particularly to a laser coagulation system adapted for use in an ophthalmological treatment in which a laser beam from a laser source is radiated into a patient's eye to develop great heat causing thermal coagulation at a predetermined portion of the biological organism in the eyeball of a patient.

2. Description of the Prior Art

There have long been known laser coagulation systems in which during an ophthalmic operation against diseases such as retina detachment, glaucoma, etc., a patient's eye is irradiated with laser energy, which is absorbed in a biological organism such as retina to develop thermal coagulation thereon for ophthalmological treatment. For this purpose, the laser coagulation system includes a laser beam projector for producing a laser beam from an argon or krypton laser, which is condensed to a laser beam of a predetermined diameter, directed toward a predetermined portion of the eyeball to be coagulated, and then focussed thereon as a laser spot for thermal coagulation.

The laser coagulation system further comprises a slit image projector for forming a slit image on the eyeball to illuminate the background and determine the portion of eyeball to be coagulated, and an observation equipment for observing the slit image and laser spot in the eyeball.

With such arrangement, the slit image projector is rotatably mounted on an instrument base about the vertical axis and includes two mirrors for directing slit light toward the patient's eye to form the slit image on the extension of the vertical axis. The laser beam projector is, on the other hand, arranged above the slit image projector and includes a mirror arranged adjacent to the two mirrors to project the laser spot in the vicinity of the slit image. The observation equipment is arranged outside of the slit image projector and mounted turnably about the vertical axis.

The mirror of the laser beam projector arranged adjacent to the mirrors of the slit image projector is displaceable or turnable vertically or horizontally by using an operating lever mechanically linked to or wire-connected to the mirror to displace or scan the laser spot in the vicinity of the slit image. This operating lever extrudes rearwardly from the observation equipment for easy access. The operating mechanism for the mirror is called a manipulator.

Such coagulation systems in the prior art have the drawbacks that the operating lever of the manipulator is mechanically dependent on the driving link or wire mechanism and disturbs the turning operation of the slit image projector or observation equipment. The manipulator is additionally provided with a spring for preventing the operating lever from falling down by gravity and returning it to a reference position. This disadvantageously makes it impossible to hold the operating lever to a position different from the reference position for a long time and to accurately displace the laser spot position in the eyeball. The operating lever is further arranged away from a control panel for controlling the instrument as a whole, thus requiring sophisticated operations.

SUMMARY OF THE INVENTION

It is, therefore, an object of the present invention to provide a laser coagulation system capable of displacing the laser spot precisely to a predetermined position to be coagulated in the eyeball of a patient.

It is another object of the present invention to provide a laser coagulation system enabling the easy turning operation of a slit image projector or observation equipment.

It is still another object of the present invention to provide a laser coagulation system capable of making the displacement of the laser spot mechanically independent from the operation of a manipulator.

According to the present invention, a laser coagulation system comprises an optical system including means for focussing a laser beam from a laser source and reflecting means for directing the focussed laser beam toward a selected portion to be coagulated in the eyeball of a patient. The laser coagulation system further comprises a manipulator for generating a desired value representative of a desired position of the reflecting means for thermal coagulation. The actual position of the reflecting means is detected and compared with the desired value from the manipulator to derive therefrom a control signal. In response to the control signal, a controller activates a driver for driving the reflecting means to displace the laser spot to a predetermined position which corresponds to the above-mentioned desired value.

With such arrangement, according to the present invention, the manipulator is operable to generate a desired valued to which the reflecting means can be set by controller and driver, thus displacing the laser spot precisely to a predetermined portion to be coagulated in the eyeball of a patient. Thus, the manipulator is not mechanically, but electrically connected with the driver and is free from the mechanical connection therewith, assuring an easy operation for the slit image projector and observation equipment.

According to the preferred embodiment, the manipulator is provided therein with an operating lever for displacing the laser spot. This allows the operating lever to be held stably in the manipulator and makes it possible for an operator to operate the manipulator without stopping the operation of the slit image projector.

BRIEF DESCRIPTION OF THE DRAWINGS

The objects and features of the present invention will become more apparent from a consideration of the following detailed description taken in conjunction with the accompanying drawings in which:

FIG. 8 is a block diagram showing an electrical arrangement of the laser coagulation system; and FIG. 9 is a flow chart showing the control flow in the laser coagulation system of the present invention.

DETAILED DESCRIPTION OF THE PREFERRED EMBODIMENTS

Figure 1:
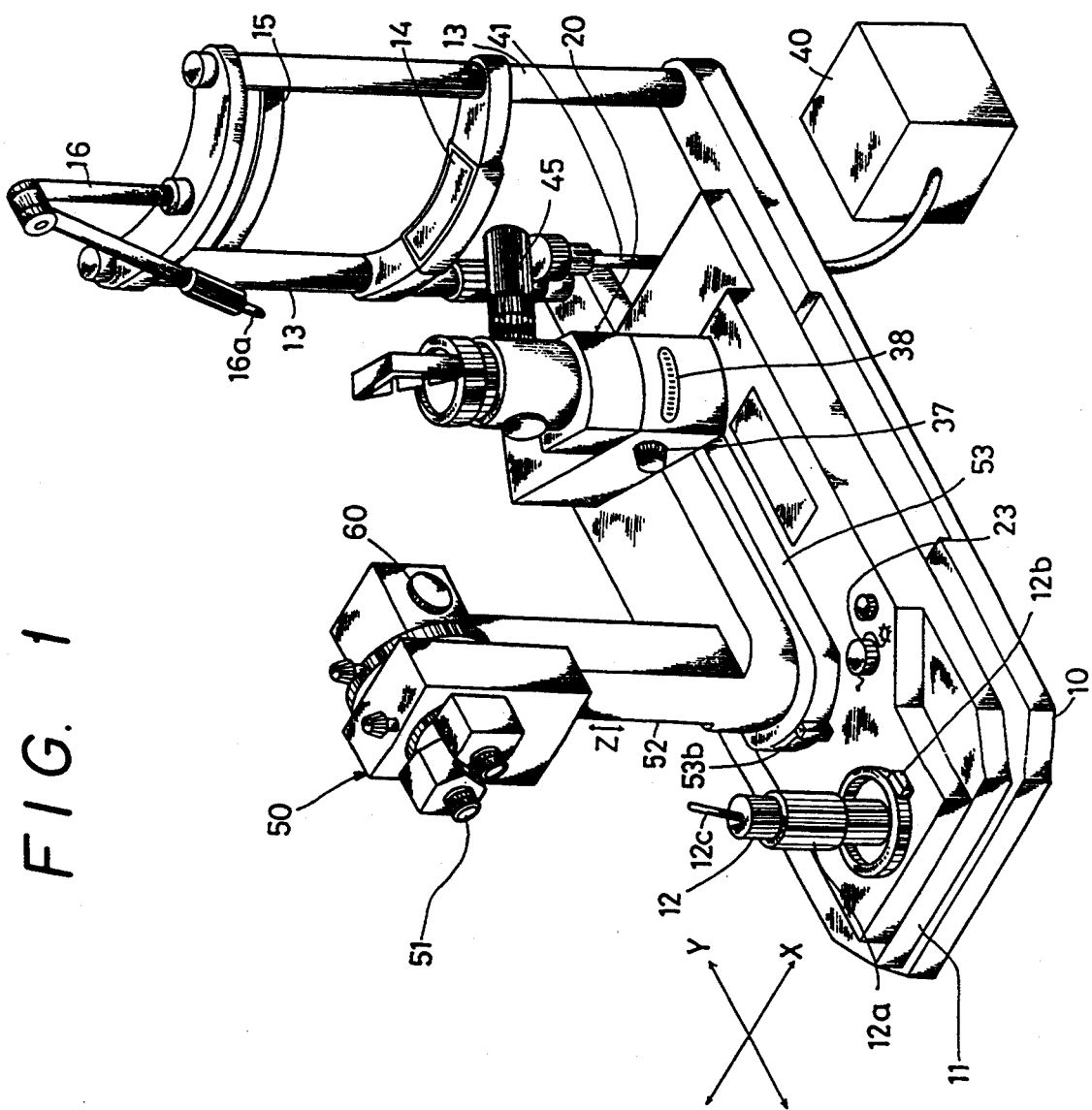
FIG. 1 is a perspective view showing an overall structure of a laser coagulation system of the present invention.

FIG. 1 shows the overall structure of a laser coagulation system according to the present invention which includes a slider 11 mounted on a base plate 10 so as to be slidable relative to the base plate 10 in a direction X and Y by means of a manipulator 12 such as a joy stick. The displacement of the slider 11 relative to the base plate 10 can be effected by operating the manipulator 12 in the directions X and Y. The slider 11 supports thereon an instrument base 53 on which a slit image projector 20, a laser beam projector 21 and an observation equipment 50 are mounted as will be fully described later. The manipulator 12 is further provided with a handle 12a, the rotation of which allows the instrument base 53 to move upwardly and downwardly to displace the projectors 20 and 21 together with the observation equipment 50 in the direction Z. Thus, the manipulator 12 can adjust the position of the instrument base 53 in the directions X, Y and Z. The thus adjusted slider 11 can be locked on the base plate 10 by means of a lock member 12b.

The base plate 10 has on its front edge two poles 13 between which a chin support 14 and a forehead pad 15 are fixedly mounted. A patient sits down in front of the apparatus with his chin against the support 14 and his forehead against the pad 15, and directs his sight to an eye fixation lamp 16a which serves to fix the patient's eye during measurement or coagulation.

Mounted on the front end of the slider 11 is the slit image projector 20 which is turnable about the axis A (see FIG. 2) and serves to project a slit image onto the eyeball to illuminate the background and determine the portion of the eye to be measured or coagulated. As will be described later, the slit image projector 20 is arranged coaxially with the laser beam projector 21 used for projecting a laser beam from a laser source 40 such as an argon or krypton laser through an optical fiber 41 onto the determined portion to be coagulated in the eyeball. The observation equipment 50 for observing the focussed laser beam and imaged slit in the eyeball is further arranged on the rear end of the slider 11 so as to be rotated about the same axis as the turning axis A for the slit image projector 20.

Figure 2:
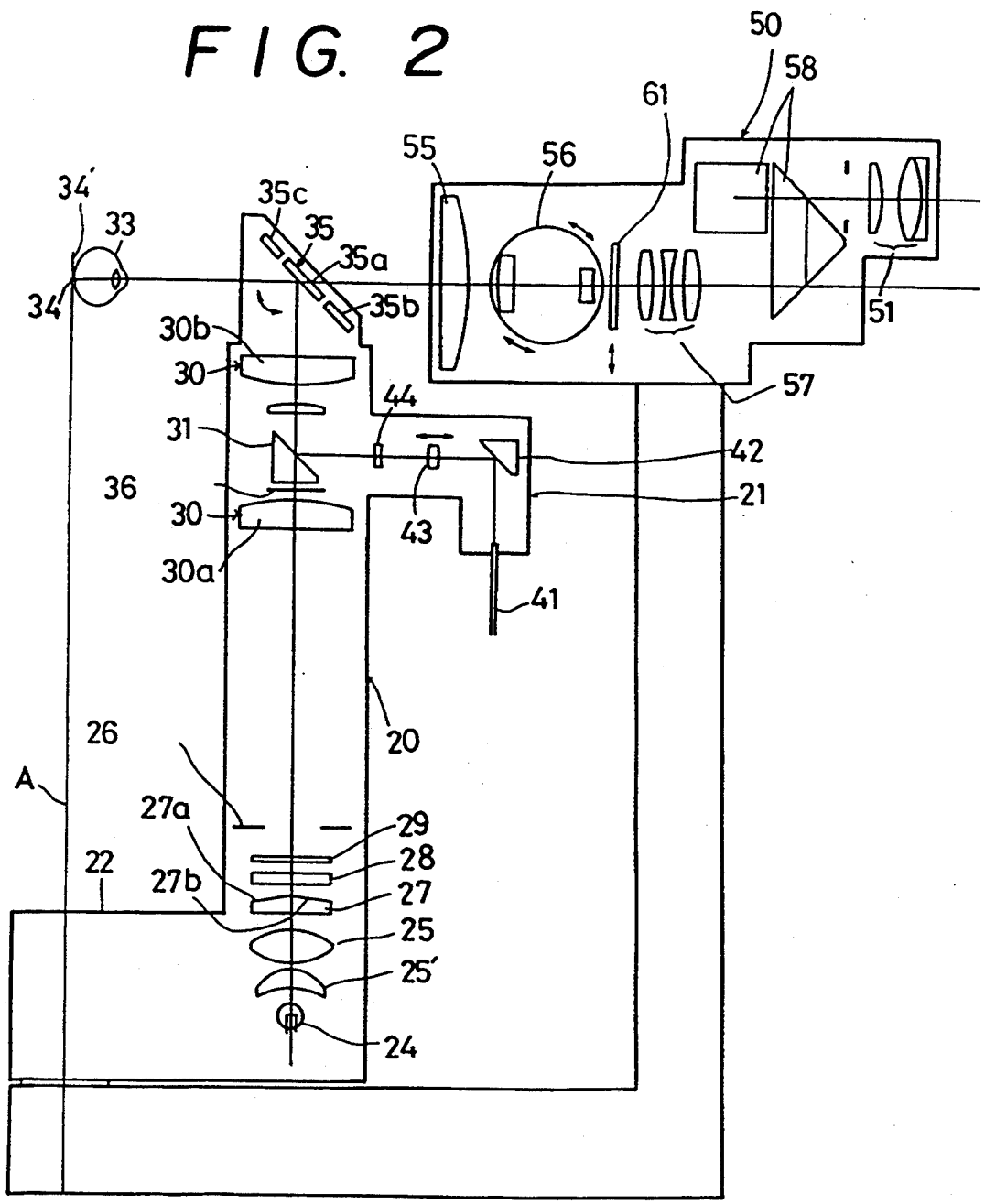
FIG. 2 is an illustrative view showing the arrangement of an optical system for a laser beam projector, slit image projector and observation equipment used in the laser coagulation system of the present invention.
Figure 3:
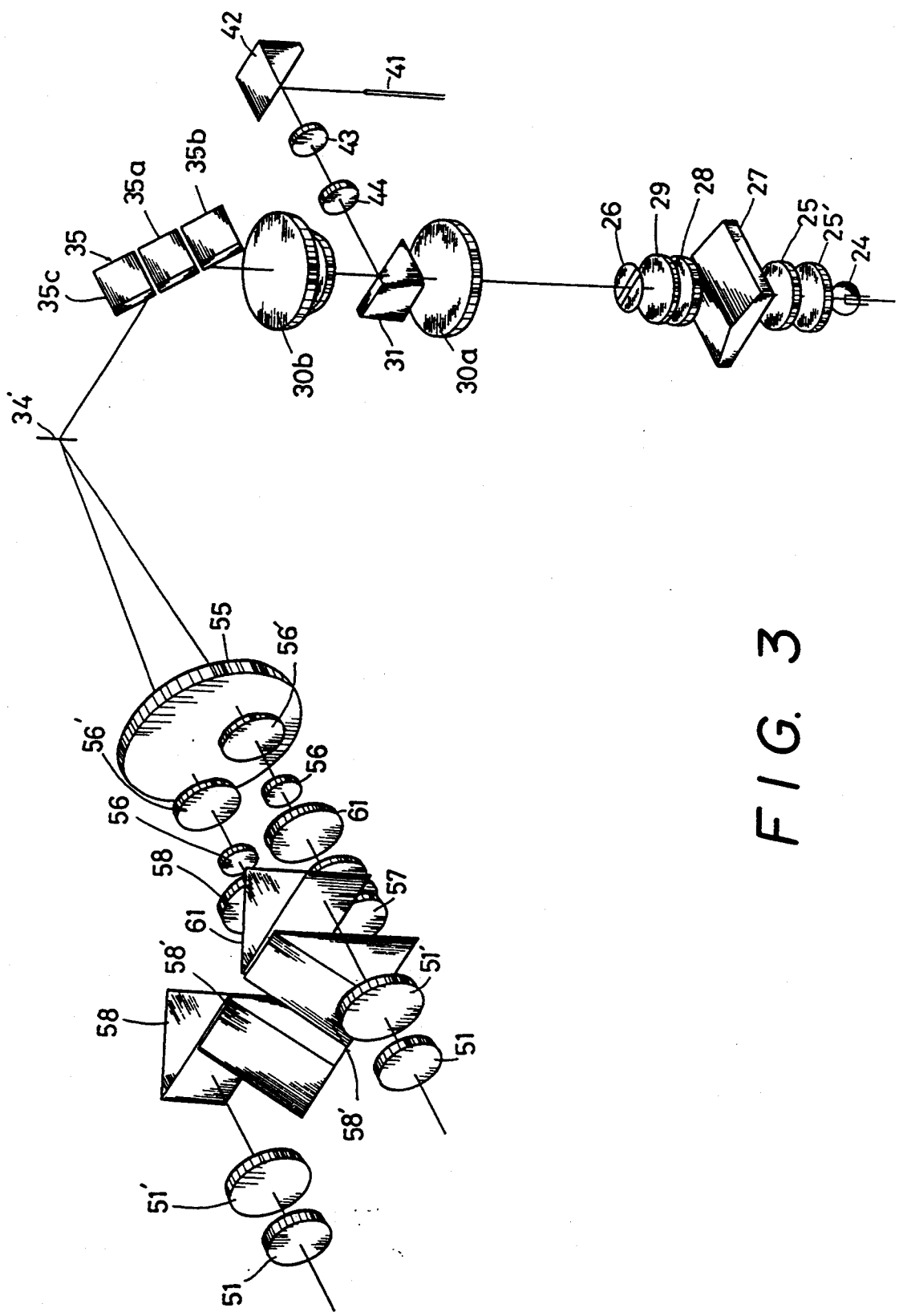
FIG. 3 is a perspective view showing the arrangement of the optical system in FIG. 2.

FIGS. 2 and 3 show the detailed arrangement of an optical system for the laser beam projector 21, slit image projector 20 and observation equipment 50. The slit image projector 20 is arranged in a housing 22 mounted so as to be rotated about the axis A and is provided therein with a lamp 24 which is adjustable in intensity by means of an adjusting knob 23 (see FIG. 1). The lamp 24 emits illuminating light, which is converged by condenser lenses 25 and 25' to illuminate a slit aperture 26. Arranged between the condenser lens 25 and slit aperture 26 are a roof-shaped deflection prism 27, an infrared ray cutting filter 28 and a detachable blue filter 29. The illuminated slit aperture 26 is imaged, for example, onto a retina 34 of a patient's eye 33 along a common optical axis as a slit image 34' by means of a focussing lens 30 including lenses 30a and 30b. To eliminate the imaging function of the eye itself, a special contact lens (not shown) is attached to the patient's eye. A mirror assembly 35 having three-divided mirror portions 35a to 35c is mounted between the patient's eye 33 and lens 30b. The central mirror portion 35a can, as described later, be turned upwardly, downwardly, leftwardly and rightwardly about respective axis perpendicular to and within the paper surface (in FIG. 2) relative to the side mirror portions 35b and 35c by means of an operating lever 12c of the manipulator 12.

Arranged between the lens 30a and a prism 31 is a screen plate 36 which serves to interrupt the arrival of the slit light to the central mirror portion 35a, while permitting it to reach the upper and lower side mirror portions 35b, 35c to the retina 34. To make the slit image on the retina 34 brighter and sharper, the deflection prism 27 has one surface 27a angled to deflect the light toward the lower mirror 35b and the other surface 27b also angled to deflect light toward the upper mirror 35c. Thus, the deflection prism functions to form the filament image of the lamp 24 at two points existing on the entrance pupil of the focussing lens 30.

It is to be noted that the slit width and length of the slit aperture 26 are adjustable by adjusting knobs 37 and 38 and the intensity of the lamp 24 are adjustable by an adjusting knob 23.

The laser beam projector 21 is, on the other hand, arranged in the same housing 22 as the slit image projector 20. The laser beam passing through the optical fiber 41 from the laser source 40 is deflected rectangularly at a prism 42 toward a variator lens 43 and a lens 44, reflected at the prism 31 and then advanced along the same common optical axis as the slit image projector 20 through the lens 30b, central mirror portion 35a and contact lens to radiate a laser spot of a predetermined diameter on the retina 34 for thermal coagulation. The spot diameter of the laser beam can be adjusted in the range of about 50 μm to 1 mm by turning a knob 45 and by adjusting the variator lens 43.

The instrument base 53 (FIG. 1) is provided with the housing 22 for accommodating the projectors 20 and 21 and a housing 52 for accommodating the observation equipment 50, and is displaceable vertically by turning the handle 12a of the manipulator 12 as mentioned before. Further, the housings 22 and 52 are turnable relative to each other about the axis A, so that the projectors 20, 21 and the observation equipment 50 can effect upward, downward and turning movement, respectively. The observation equipment 50 includes an optical system comprised of an objective 56, variator lenses 55 and 56', a safety filter 61, a focussing lens 57, erecting prisms 58 and 58', and eyepieces 51, 51'. The observation equipment 50 allows the observation of the slit image and laser beam spot formed in the eyeball. The adjustment of a knob 60 causes the variator lens 56 to be adjusted to provide an enlarged or reduced slit image or laser beam spot. The safety filter 61 is used to interrupt the laser beam reflected back from the irradiated portion of eye or cornea and protect the eyes of an observer. For this purpose, the safety filter 61 is automatically inserted into the optical path of the observation equipment 50 immediately before the laser source 40 is activated to produce a stronger laser beam.

It should be noted that, as shown in FIG. 3, the optical elements following the objective 55 are provided in pairs respectively to allow binocular observation.

Figure 4:
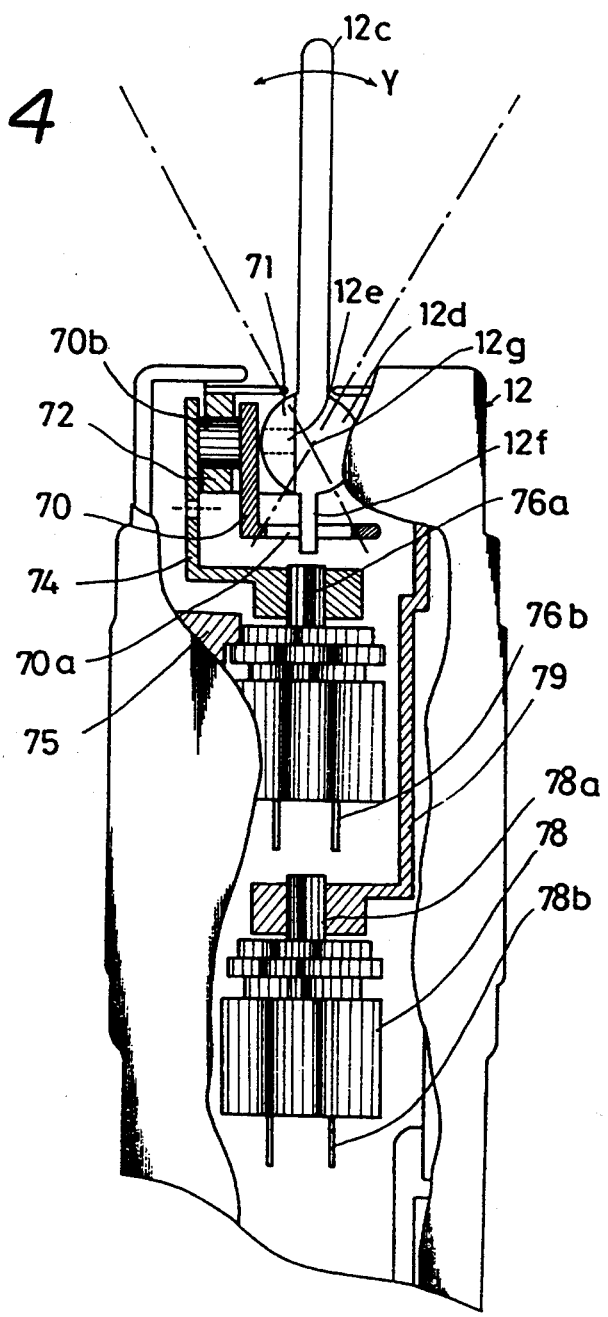
FIG. 4 is a side view showing the inner construction of a manipulator for the laser coagulation system of the present invention.
Figure 5:
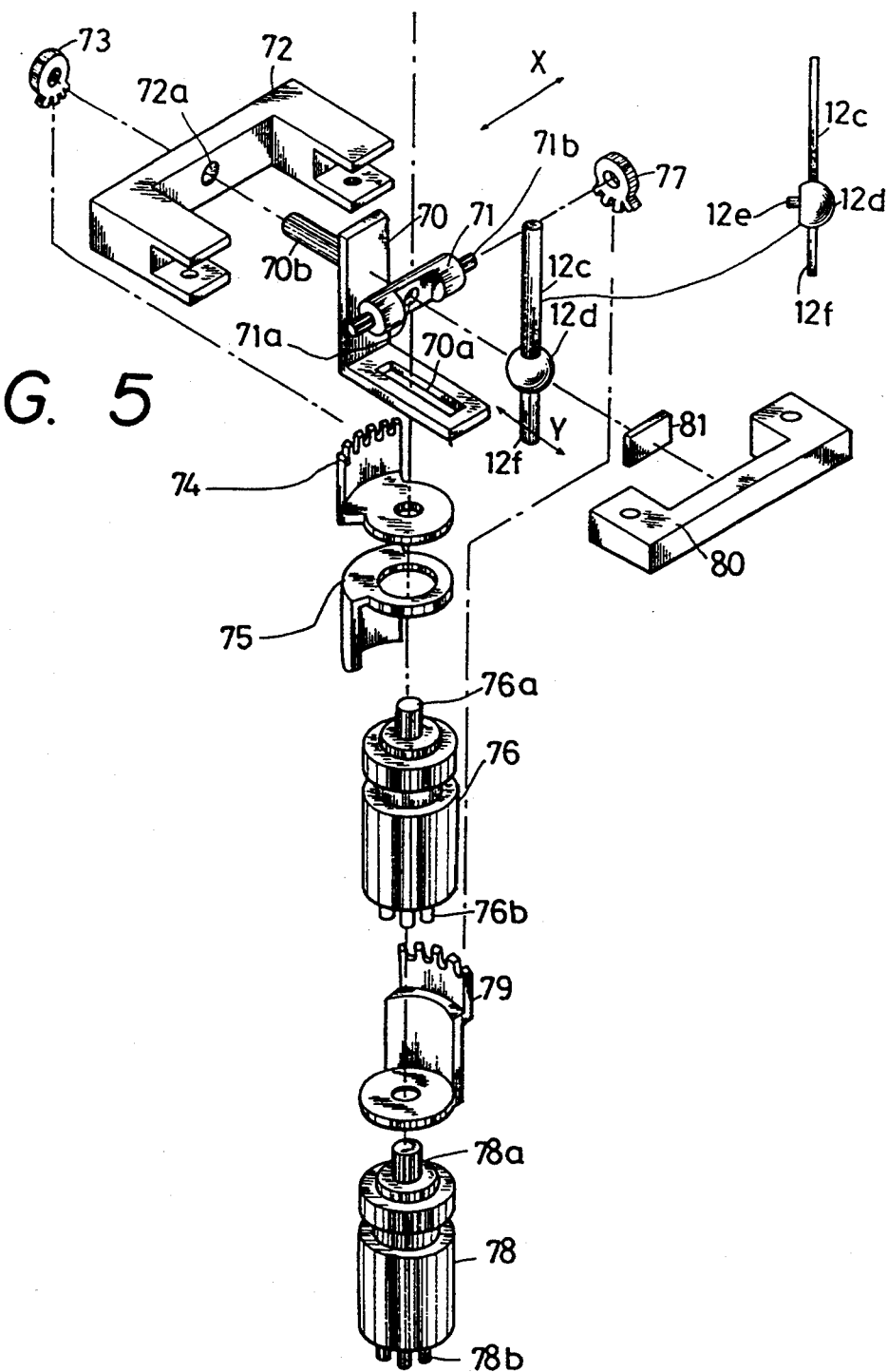
FIG. 5 is a perspective view showing the manipulator in FIG. 4 in a disassembled state.

FIGS. 4 and 5 show the detailed construction of the manipulator 12 which includes the operating lever 12c having a spherical portion 12d, provided with a pin 12e inserted into a hole 71a in a cylindrical member 71. The operating lever 12c has its lower part 12f brought into engagement with a cut-out portion 70a of an L-shaped lever 70. This lever 70 is provided with a pin 70b which intrudes into a hole 72a in a C-shaped block 72 fixedly mounted in the housing for connection with a pinion gear 73. Thus, the turning of the operating lever 12c in the direction X in FIG. 5 causes the L-shaped lever 70 to be swung about the pin 70b to rotate the pinion gear 73 and a crown gear 74 engaging therewith. The turning of the crown gear 74 allows the rotation of the shaft 76a of an X-potentiometer 76 held in a holder 75, so that the displacement of the operating lever 12c in the direction of X can be converted into an electrical signal through a terminal 76b of the X-potentiometer 76.

To the shaft 71b of the cylindrical member 71, there is fixed a pinion gear 77 which engages with a crown gear 79 fixed to the shaft 78a of a Y-potentiometer 78. When the operating lever 12c is displaced into the direction Y perpendicular to the direction X, the L-shaped lever 70 can be turned about the center 12g within the range defined by the cutout 70a. This allows the shaft 78a of the Y-potentiometer 78 to be turned, thereby converting the displacement of the operating lever 12c in the direction Y into a corresponding signal through its terminal 78b.

It is to be noted that an elastic member such as a spring plate 81 is provided to cooperate with a block 80 to urge the operating lever 12c leftwardly.

Figure 6:
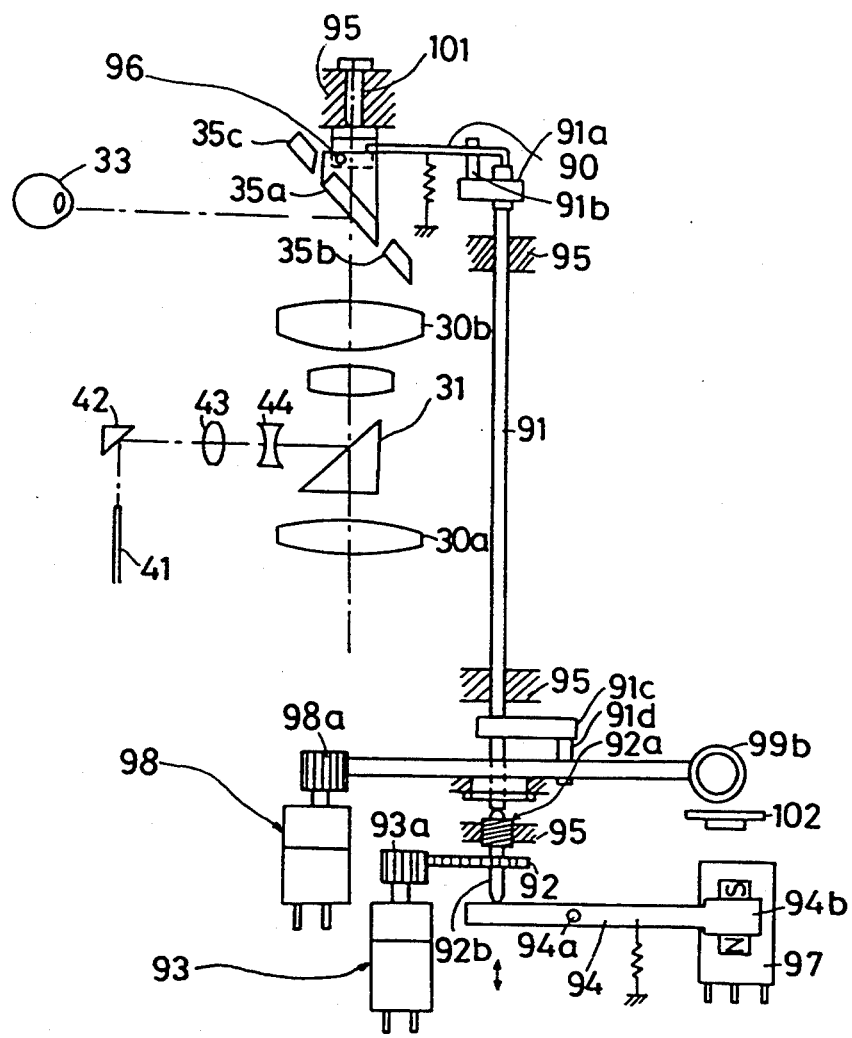
FIG. 6 is a side view showing the arrangement of a driving mechanism for displacing a mirror in a laser beam projector together with detectors for detecting the actual position of the mirror.
Figure 7:
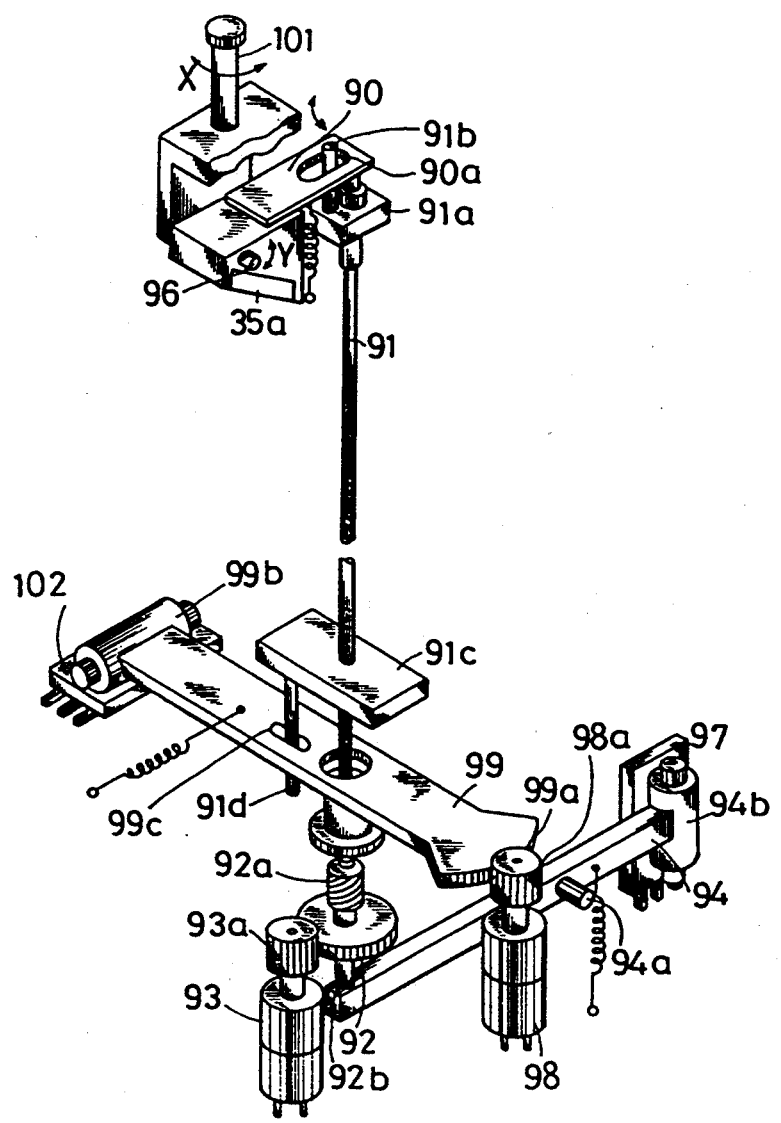
FIG. 7 is a perspective view showing the arrangement of the driving mechanism corresponding to that in FIG. 6.

FIGS. 6 to 8 show the mechanical and electrical arrangement for converting the displacement of the operating lever 12c into the electrical signal to control the central mirror portion 35a to a desired position.

In FIGS. 6 and 7, the center mirror portion 35a abuts against one end of a mirror lever 90 urged downwardly by a spring. The mirror lever 90 is connected at the other end with one end of an interconnecting rod 91 which is rotatably mounted in a housing 95 and the other end of which is connected to a gear 92 provided with a helicoid screw 92a. The gear 92 engages with the pinion gear 93a of a Y-directional motor 93 (DC motor with reduction gears) and abuts at its lower end 92b on one end of a detection lever 94 which bears a magnet 94b at its other end and which is mounted rotatably about an axis 94a. A spring is attached to the detection lever 94 to urge it to come into contact with the end 92b of the gear shaft. The activation of the Y-directional motor 93 causes the rotation of the pinion gear 93a to displace the helicoid gear 92a due to the engagement of the gear 92 with the pinion gear 93a, thereby displacing the interconnecting rod 91 vertically to rotate the mirror 35a about an axis 96 as shown in FIG. 7 by a double arrow Y. The detection lever 94 turns about the axis 94a as the central mirror portion 35a rotates about the axis 96. This causes the displacement of the magnet 94b relative to a Hall element 97 and allows the indirect detection of the turning movement of the central mirror portion 35a.

The interconnecting rod 91 is further provided at one end with a lever 91a having a pin shaft 91b inserted into a longitudinal slot 90a formed in the mirror lever 90 and also provided at the other end with a lever 91c having a pin shaft 91d coming into engagement with a longitudinal slot 99c formed on a lever 99. The lever 99 is urged by a spring to absorb the backlash of gear engagements.

An X-directional motor 98 having a construction similar to the Y-directional motor 93 is provided for turning displacement of the mirror portion 35a about the other axis. The motor 98 has a pinion gear 98a engaging in a rack of teeth 99a on a lever 99. The operation of the directional X motor 98 causes the lever 99 supported in a housing 95 to rotate about the same axis as the interconnecting rod 91 to turn the mirror portion 35a horizontally about a shaft 101 in the direction of the double arrow X because the pin shaft 91b engaging with the mirror lever 90 rotates about the axis of the rod 91. The turning displacement of the mirror portion 35a about the shaft 101 can be detected by a Hall element 102 relative to which a magnet 99b provided on the other end of the lever 99 is displaced as the mirror portion 35a turns about the shaft 101.

As shown in FIG. 8, the displacement of the operating lever 12c in the direction X is detected by the X-potentiometer 76, an instruction signal from which is applied to an analog-to-digital converter 112 in a controller 111 through an amplifier 110 and converted into a digital signal. The displacement of the mirror portion 35a in the direction X is, on the other hand, detected by the Hall element 102, a signal from which is similarly fed to the analog to digital converter 112 for digital conversion. The analog-to-digital converter 112 is connected to a storage circuit 114 for storing the desired value or data corresponding to the instruction signal of the operating lever 12c and the actual or current position data of the mirror portion 35a detected by the Hall element 102. Both the desired and actual data are compared by a comparator 115 to derive therefrom a deviation. In response to the deviation, a CPU 116 generates a control signal, which is applied to a driver 117 to drive the X-directional motor 98 and rotate the mirror portion 35a until the deviation disappears. An interface 117 is connected to the controller 111 for the interface between the controller 111 and an external device.

In FIG. 8, there is shown only the control system for the direction X. It will, however, be appreciated that a control system for the direction Y can be arranged similarly to the control system for the direction X to thereby effect the two-dimensional control.

The operation of the laser coagulation system according to the present invention will now be described in connection with FIG. 9.

The patient first sits down with his chin against the support 14 and his forehead against the pad 15 and direct his sight to the eye fixation lamp 16. The lamp 24 of the slit image projector 20 is then turned on to form the slit image 34' on the retina 34 of the patient's eye 33 through the contact lens set thereon. The slit light has its central flux inhibited to arrive at the central mirror portion 35a by means of the screen plate 36 and is reflected only at the upper and lower portions 35b and 35c to form the slit image 34' on the retina 34. In this case, the deflection prism 27 is used to deflect the slit light towards the side mirror portions 35b and 35c effectively. The intensity of the slit image can be adjusted by the knob 23, and the slit width and length can be adjusted by the adjusting knobs 37 and 38.

If the slit image 34' deviates from the desired place in the above-mentioned slit image formation, the manipulator 12 may be operated to displace the slider 11 and the housings 22 and 52 in the directions X, Y and Z and turn the projectors 20, 21 or observation equipment 50 about the axis A relative to each other until the slit image is formed on the desired portion for coagulation.

The thus formed slit image 34' can be observed by the optical system of the observation equipment 50 including the objective 55, variator lens 56, imaging lens 57, erecting prism 58 and eyepiece 51. After the portion of eye to be coagulated has been determined and selected, the laser source 40 is activated to emit a week laser beam, which is caused to pass through the prism 42, variator lens 43, lens 44, prism 31, and lens 30b, reflected at the central mirror portion 35a and then focussed as a spot onto the retina 34. For coagulation, a stronger laser beam is generated from the laser source 40 by changing power. When the stronger beam is activated, the safety filter is automatically inserted into the optical path of the observation equipment 50 to protect the eyes of the observer from the laser beam reflected from the irradiated portion of the patients eye or retina.

For fine and precise coagulation, the laser spot on the retina 34 can be scanned by displacing the central mirror portion 35a vertically or horizontally, that is, in the direction X or Y by means of the operating lever 12c of the manipulator 12.

The displacement of the operating lever 12c in the direction X, for example, in FIG. 5 (Step S1 in FIG. 9) causes the shaft 76a of the X-potentiometer 76 to rotate due to the engagement of the pinion gear 73 with the crown gear 74. This allows an analog signal representative of a desired value for location of the laser beam spot to be produced from its terminal 76b. This analog signal is amplified by the amplifier 110 (FIG. 8), converted into the digital signal by the analog-to-digital converter 112 and then stored in the storage circuit 114. The signal corresponding to the position of the operating lever 12c is always stored in the storage circuit 114 successively. Thus, the renewed operation of the lever 12c provides a new desired value different from the preceding one. This difference is calculated in terms of magnitude and sign by the comparator 115 in the controller 111(Step S2).

This calculation results in the formation of a deviation signal, which is applied to the driver 117 to drive the X-directional motor 98 (Step S3) to rotate the lever 99 and the pin shaft 91b about the axis of the rod 91. This causes the turning of the mirror portion 35a about the shaft 101 and the scanning of the laser spot in the direction X. The actual position of the mirror portion 35a detected by the Hall element 102 is stored in the storage circuit 114, and compared with the preceding positional signal to derive therefrom the deviation. This activates the motor 98 which displaces the mirror portion 35a in the direction X until it reaches the new desired position determined by the operation of the lever 12c and the deviation disappears(Steps S4 and S5).

These procedures apply also for the displacement of the laser spot in the direction Y. The displacement of the operating lever 12c in the direction Y causes the Y-potentiometer 78 to produce a desired value, which is compared with the actual signal representative of the position of mirror portion 35a obtained from the Hall element 97 to derive therefrom a control signal. This causes the Y-directional motor 93 to be driven to rotate the mirror portion 35a about the axis 96 by means of the interconnecting rod 91. This continues until the mirror portion 35a reaches the desired position.

It should be noted that the mirrors as mentioned above are realized as reflecting means, and therefore include all kinds of reflectors such as total reflection mirrors, half mirrors or reflecting surfaces of prisms.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

We claim:

1. A laser coagulation system for use in an ophthalmological treatment in which a laser beam is radiated into the eyeball of a patient to develop heat causing thermal coagulation at a selected portion in the eyeball, the system comprising:

a slit image projector for projecting a slit image into the eyeball of a patient to determine a selected portion of the eyeball to be coagulated;

a laser beam projector for projecting a laser beam into the selected portion of the eyeball to be coagulated;

wherein both of said projectors include a common reflecting means for directing the slit image or the laser beam toward the selected portion of the eyeball, said reflecting means being divided into side portions for directing the slit image toward said selected portion and a central portion for directing the laser beam toward said selected portion, the central portion of said reflecting means being movable relative to the side portions thereof to displace the laser beam relative to the slit image;

the slit image projector including a slit aperture for producing slit light, a condenser lens for condensing the slit light, and a deflection prism arranged between the slit aperture and the condenser lens and having a roof-shaped surface one half of which serves to deflect the slit light toward one side portion of the reflecting means and the other half of which serves to deflect the slit light toward the other side portion thereof;

detecting means for detecting the actual position of the central portion of said reflecting means to determine an actual value representative of said actual position;

a manipulator for inputting a desired value representative of a desired position of the central portion of said reflecting means;

controller means for generating a control signal in response to a deviation of said actual value from said desired value; and driving means responsive to said control signal for displacing the central portion of said reflecting means until said laser beam reaches a predetermined position corresponding to said desired value where said deviation disappears.

2. A laser coagulation system as set forth in claim 1; wherein the controller means includes an analog-to-digital converter for converting said desired and actual values into respective digital signals, a storage circuit for storing the digital signals, and a comparator for comparing the digital signals with each other to derive therefrom said control signal.

3. A laser coagulation system as set forth in claim 1; wherein said detecting means comprises a Hall element and a magnet mounted to move corresponding to the displacement of said reflecting means central portion relative to the Hall element, thereby causing the Hall element to determine said actual value representative of the actual position of said reflecting means central portion.

4. A laser coagulation system as set forth in claim 1; wherein said manipulator includes a movable operating lever, the operation of which determines said desired value.

5. A laser coagulation system as set forth in claim 4; wherein said manipulator includes at least one potentiometer for converting a mechanical movement of said operating lever into an electrical signal representative of said desired value effective to specify the location of the focussed laser beam position.

6. A laser coagulation system as set forth in claim 4; wherein said operating lever is displaceable in a first direction and in a second direction perpendicular to said first direction to displace said reflecting means in said first and second directions.

7. An apparatus for ophthalmic laser treatment of the eye of a patient, comprising: slit image projecting means for projecting a slit image along a common optical axis into the eye of a patient to illuminate the eye to enable a determination as to the portion of the eye to be treated, the slit image projecting means including a source of light, and means for forming the light from the light source into a slit image composed of two slit image components; laser beam projecting means for projecting a laser beam spot along the common optical axis into the eye of the patient to treat the eye; a common reflecting means disposed on the common optical axis for selectively reflecting the slit image and the laser beam spot toward the eye, the common reflecting means having two side portions positioned to reflect and direct the respective slit image components toward the eye to illuminate the eye, and and a central portion drivably displaceable relative to the two side portions to reflect and direct the laser beam spot toward the eye to treat the eye; observing means for observing the slit image and the laser beam spot projected into the eye of the patient to determine the portion of the eye to be treated with reference to the slit image; and operating means operative while the laser beam spot is being observed for driving the central portion of the reflecting means to effect scanning movement of the laser beam spot within the determined portion of the eye to carry out the ophthalmic laser treatment, the operating means including driving means for driving the central portion of the common reflecting means according to a control signal, mounting means driveable by the driving means for mounting the central portion of the reflecting means to undergo displacement along at least one axis relative to the two side portions to effect the scanning movement of the laser beam spot on the eye, detecting means operative during scanning of the laser beam spot for detecting the current position of the central portion of the common reflecting means representative of the current position of the laser beam spot to produce a corresponding current data effective to control the scanning of the laser beam spot, and control means for comparing the current data and instruction data corresponding to a desired position with each other to produce the control signal effective to determine an amount of displacement of the central portion of the common reflecting means needed to displace the same from the current position to the desired position.

8. An apparatus according to claim 7; wherein the mounting means includes means for mounting the central portion to undergo angular displacement around the common optical axis and another axis perpendicular to the common optical axis to thereby enable two-dimensional scanning of the laser beam spot.

9. An apparatus according to claim 7; wherein the detecting means comprises a stationary Hall effect element and a magnetic element mounted for movement with the central portion of the common reflecting means relative and adjacent to the Hall effect element.

10. An apparatus according to claim 7; wherein the control means includes a comparator for comparing the current data and instruction data with each other to determine the difference therebetween.

11. An apparatus according to claim 7; wherein the driving means includes a motor driven to rotate according to the control signal, and a mechanical linkage for transmitting the motor rotation to the central portion of the common reflecting means.

12. An apparatus according to claim 7; wherein the control means includes an analog-to-digital converter for converting the instruction data and current data into respective digital signals, a storage circuit for storing the digital signals, and a comparator for comparing the digital signals with each other to drive therefrom the control signal.

13. An apparatus according to claim 7; wherein the operating means includes input means manually operative during observation of the laser beam spot by the operator for inputting the instruction data indicative of a desired position of the central portion of the common reflecting means and effective to scan the laser beam spot to the desired position.

14. An apparatus according to claim 13; wherein the input means comprises a manually two-dimensionally movable operating lever, and a potentiometer for converting the two-dimensional movement of the operating lever into an instruction data.

* * * * *